United States Patent [19]

Bermes et al.

[11] Patent Number: 6,160,169
[45] Date of Patent: Dec. 12, 2000

[54] PREPARATION OF AMINE SALTS OF 4-NITROTOLUENE-2-SULFONIC ACID

[75] Inventors: Rudolf Bermes, Ludwigshafen; Armin Haag, Hirschberg; Hellmut Kast, Bobenheim-Roxheim; Peter Krötzsch, Ketsch, all of Germany

[73] Assignee: BASF Aktiengesellschaft, Ludwigshafen, Germany

[21] Appl. No.: 09/206,340

[22] Filed: Dec. 7, 1998

[30] Foreign Application Priority Data

Dec. 13, 1996 [DE] Germany ............... 196 51 804

[51] Int. Cl.⁷ .................................................. C07C 309/00
[52] U.S. Cl. ................................. 562/58; 534/728
[58] Field of Search ................... 562/58; 534/728

[56] References Cited

U.S. PATENT DOCUMENTS

| | | | |
|---|---|---|---|
| 2,378,168 | 6/1945 | Witte | 562/73 |
| 3,840,591 | 10/1974 | Lee et al. | 562/63 |
| 4,310,323 | 1/1982 | Arsac et al. | 8/527 |
| 4,310,331 | 1/1982 | Arsac et al. | 8/527 |
| 4,382,039 | 5/1983 | Goldschmitt et al. | 562/73 |
| 4,560,745 | 12/1985 | Weberndoerfer et al. | 534/728 |
| 4,617,380 | 10/1986 | Hinson et al. | 534/728 |
| 4,617,381 | 10/1986 | Hinson et la. | 534/728 |
| 4,803,017 | 2/1989 | Bugner et al. | 562/73 |
| 4,922,008 | 5/1990 | Seifert et al. | 562/58 |
| 4,948,702 | 8/1990 | Wallbillich et al. | 430/271.1 |
| 5,026,830 | 6/1991 | Langfeld et al. | 534/728 |
| 5,041,539 | 8/1991 | Tzikas et al. | 534/728 |

FOREIGN PATENT DOCUMENTS

| | | |
|---|---|---|
| 0 041 134 | 12/1981 | European Pat. Off. . |
| 0 534 360 | 3/1993 | European Pat. Off. . |
| 30 46 450 | 8/1981 | Germany . |
| 43 11 373 | 10/1994 | Germany . |

*Primary Examiner*—Paul J. Killos
*Assistant Examiner*—Taylor V Oh
*Attorney, Agent, or Firm*—Oblon, Spivak, McClelland, Maier & Neustadt, P.C.

[57] ABSTRACT

A process for preparing amine salts of 4-nitrotoluene-2-sulfonic acid by sulfonation of nitrotoluene with oleum, subsequent dilution of the reaction mixture with water and extraction with lipophilic amines, wherein the acidic aqueous solution of the sulfonation product is partially neutralized with mineral bases.

The compounds prepared according to the invention are particularly suitable for preparing dyes.

4 Claims, No Drawings

PREPARATION OF AMINE SALTS OF 4-NITROTOLUENE-2-SULFONIC ACID

The present invention relates to a process for preparing amine salts of 4-nitrotoluene-2-sulfonic acid by sulfonation of nitrotoluene with oleum, subsequent dilution of the reaction mixture with water and extraction with lipophilic amines, and to amine salts of 4-nitrotoluene-2-sulfonic acid, their use for preparing dyes, and to a process for preparing Direct Yellow 11 (C.I. 40000).

European Patent 0041134 discloses a process for removing water-soluble salts of aromatic sulfonic acids from sulfonation mixtures in which the sulfonation mixtures are extracted as dilute aqueous solutions with lipophilic amines, there being formation of amine salts of the aromatic sulfonic acids.

The disadvantages of this process are that large losses of these substances may occur in some cases, depending on the amine, and that moreover the aromatic sulfonic acids cannot be extracted quantitatively.

It is an object of the present invention to provide a more commercial process which does not have the disadvantages described above.

We have found that this object is achieved in that the amine salts of 4-nitrotoluene-2-sulfonic acid are obtained in a better yield and with smaller amine losses when the acidic aqueous solution of the sulfonation product is partially neutralized with mineral bases.

4-Nitrotoluene-2-sulfonic acid is obtained in a manner known per se as the product of the sulfonation of 4-nitrotoluene with oleum. Sulfonation of 4-nitrotoluene with oleum is described, for example, in Beilsteins Handbuch der Organischen Chemie, Fourth Edition, Volume 11, page 90.

The product obtained from the sulfonation is first diluted with ice and water, expediently adjusting the sulfuric acid concentration to from 15 to 65% by weight, preferably 30 to 50% by weight.

The partial neutralization of the sulfuric acid with mineral bases, preferably 50 to 70% of the acid, is then carried out according to the invention. Suitable bases are mineral bases such as alkali metal and alkaline earth metal hydroxides, for example lithium hydroxide and calcium hydroxide, in particular potassium hydroxide and sodium hydroxide. The bases can be employed either as solid or in aqueous solution. The partial neutralization is most simply carried out by adding sodium hydroxide solution. It is expedient, in view of the volume to be handled, to employ maximized concentrations. The concentration of nitrotoluene-sulfonic acid varies from about 10 to 30% of the weight of the partially neutralized aqueous solution.

The acidic aqueous solution is then extracted with the lipophilic amine(s), whereupon the 4-nitrotoluene-2-sulfonic acid is transferred into the amine phase. It is immaterial in this connection whether the lipophilic amine is added before or after the partial neutralization. However, the extraction and the mixing associated therewith take place subsequently.

The amines used for the extraction should be substantially insoluble in the aqueous medium which is present. By lipophilic amines are meant amines which are insoluble or substantially insoluble in water. They should have sufficient lipophilicity as amine salts of 4-nitrotoluene-2-sulfonic acid to separate from the aqueous phase.

Suitable for the extraction are, for example, secondary and, preferably, tertiary amines having 12 to 36 carbon atoms, preferably $C_4$–$C_2$-alkylamines such as tributylamine, triamylamine, dicylohexylamine, trihexylamine, di-2-ethylhexylamine, methyldi-2-ethylhexylamine, butyldi-2-ethylhexylamine, tri-2-ethylhexylamine, tri-n-octylamine or methyldidodecylamine.

It is particularly advantageous to use di-2-ethylhexyl-, tributyl-, triamyl-, trihexyl- or tri-2-ethylhexylamine. The ammonium salts formed by these amines with 4-nitrotoleune-2-sulfonic acid are moreover novel.

Besides pure amines, it is also possible to use mixtures.

The lipophilic amines are generally employed in an amount which is at least stoichiometric relative to the sulfonic acid.

The lipophilic amine salts can be prepared over a wide range of temperature of from −10 to 130° C., preferably at 20–90° C.

After the extraction, the amine solution generally still contains small amounts of sulfuric acid, which can be removed by washing one or more times with water. Whether removal of residual sulfuric acid is necessary depends on the intended use of the lipophilic amine salts prepared according to the invention.

The amine salts prepared according to the invention are preferably used to prepare the dyes Direct Yellow 11 (C.I. 40000) and Direct Orange (C.I. 40002 and 40003). Conversion into the dyes is known in principle, but preparation from the amine salts has advantages on use of the known methods (see, for example, DE-A 3 046 450).

If it is wished to use the amine salts directly in the condensation reaction for the dye, it is necessary to adjust to the alkaline aqueous medium necessary for the condensation, as a rule using aqueous alkali metal hydroxide solutions such as lithium hydroxide solution or, preferably, sodium hydroxide solution.

In the condensation which takes place in the alkaline aqueous medium, the lipophilic amines are liberated again from the amine salts and can be removed and reused. However, it may be more expedient initially not to remove the lipophilic amines but, on the contrary, to carry out the condensation in their presence and subsequently to use them, after acidification of the reaction solution, directly for extracting the dye which is formed. This results in the dyes as amine salts which are substantially free of extraneous salts and are outstandingly suitable for conversion into water-miscible liquid formulations, for example by treating the lipophilic dye-amine salts with water-miscible amines in aqueous solution.

In a preferred variant of the process, the dye Direct Yellow 11 (C.I. 40000) is prepared by
a) making the solution, prepared in the process according to the invention, of the 4-nitrotoluene-2-sulfonic acid in the amine basic with aqueous alkali metal hydroxide solution,
b) heating the mixture to from 50 to 100° C.,
c) subsequently acidifying and, after thorough mixing and phase separation, removing the aqueous phase and
d) extracting the dye which is present in the organic phase with water and water-miscible amines, removing the aqueous phase, neutralizing, and isolating the dye present therein where appropriate.

The hydrophilic amine salts produced in this way have, especially in the absence of extraneous salts, excellent solubility in water and make it possible to prepare highly concentrated dye solutions which may also contain other water-miscible solvents.

Examples of suitable water-miscible amines are mono-, di- or triethanolamine, mono- and dipropanolamine, methyldiethanol- or dipropanolamine, butyldiethanolamine or diethylethanolamine.

Water-miscible solvents are preferably glycols and glycol ethers and amides. Examples which may be specifically mentioned are di-, tri- or tetraethylene glycol, propylene glycol, dipropylene glycol, butyldiglycol, methoxypropanol, butanediol, neopentyl glycol, urea, dimethylformamide, N-methylpyrrolidone or ε-caprolactam.

The dyes C.I. 40000, 40002 and 40003 are preferably used for coloring paper. Parts and percentages in the following examples are by weight unless otherwise noted.

EXAMPLE 1

137 parts of 4-nitrotoluene are melted at 55 to 60° C. and stirred during dropwise addition of 395 parts of 24% oleum. The temperature is then raised to 70° C., and stirring is continued at this temperature for one hour. When the sulfonation is complete, the mixture is cooled and slowly added to 500 parts of water. At 85° C., 360 parts of tri-2-ethylhexylamine are added, and the mixture is stirred at 80° C. while 300 parts of 50% strength sodium hydroxide solution are added in one hour. The mixture is allowed to settle, and the lower acidic aqueous phase is removed while still hot. The amine phase is stirred with 1000 parts of water at 70 to 80° C. for 15 minutes; after settling, 1026 parts of water are removed at 45° C. When the amine phase is stirred with 300 parts of water and 24 of lithium hydroxide, the mixture warms up to 40° C; the alkali and the 4-nitrotoluene sulfonic acid dissolve in the aqueous phase, from which 357 parts of tri-2-ethylhexylamine are removed and recovered.

The aqueous solution of lithium 4-nitrotoluenesulfonate is mixed with a further 200 parts of water and 12 parts of lithium hydroxide, heated to 56 to 60° C. and stirred at 60° C. for a further 8 hours, during which the nitrotoluenesulfonic acid is condensed to give the dye. Finally, the mixture is diluted with 500 parts of water and 12 parts of acetic acid to result in 1262 parts of a concentrated solution of the dye C.I. Direct Yellow 11.

EXAMPLE 2

Replacing the tri-2-ethylhexylamine used in Example 1 by 246 parts of di-2-ethylhexylamine and proceeding similarly results in a liquid formulation of the dye C.I. Direct Yellow 11 in similar quality and yield.

EXAMPLE 3

Carrying out the procedure of Example 1 but using 270 parts of trihexylamine in place of the tri-2-ethylhexylamine results in a concentrated solution of the dye C.I. Direct Yellow 11 in similar yield and quality.

EXAMPLE 4

Carrying out the procedure of Example 1 but using 230 parts of triisoamylamine in place of the tri-2-ethylhexylamine results in an equally good liquid formulation of the dye C.I. Direct Yellow 11 in similar yield.

EXAMPLE 5

137 parts of 4-nitrotoluene are sulfonated with oleum as indicated in Example 1, added to 500 parts of water and mixed with 190 parts of tributylamine at 60 to 80° C.

360 parts of 50% strength sodium hydroxide solution are added, the mixture is stirred at 85° C. for 30 minutes, and the stirrer is switched off. After settling, the partially neutralized lower aqueous phase is removed, 1600 parts of fresh water and 350 parts of 50% strength sodium hydroxide solution are added, and the mixture is slowly heated to 56 to 58° C. The condensation is completed by stirring at the same temperature for 4 hours, followed by cooling. While cooling, about 280 parts of 96% strength sulfuric acid are added to adjust the pH to about 1. The resulting mixture is refluxed for one hour. After cooling to about 95° C., the stirring is stopped and settling is allowed to take place for one hour; the acidic aqueous phase is then removed (about 2250 parts). 650 parts of water and 198 parts of diethanolamine are added to the remaining organic phase and, after refluxing for 45 minutes, it is allowed to settle again. Two phases are obtained, the lower being the dye solution, which is drained off, and the upper being 174 parts of colorless tributylamine. The dye phase is neutralized with 161 parts of 20% strength sulfuric acid to result in 1268 parts of a concentrated solution of the dye C.I. Direct Yellow 11.

EXAMPLE 6

Carrying out Example 5 using 275 parts of trihexylamine in place of the tributylamine results in the same yield of a concentrated solution of the dye C.I. Direct Yellow 11 and recovery of 259 parts of trihexylamine.

We claim:

1. A method of preparing the dye Direct Yellow 11 (C.I. 40000), comprising:
   a) sulfonating nitrotoluene with oleum, thereby preparing 4-nitrotoluene-2-sulfonic acid;
   b) diluting the solution containing said 4-nitrotoluene-2-sulfonic acid with water;
   c) partially neutralizing the 4-nitrotoluene-2-sulfonic acid to 50–70% neutralization with added mineral base;
   d) extracting the partially neutralized 4-nitrotoluene-2-sulfonic acid with a lipophilic amine;
   e) basefying the extracted, partially neutralized 4-nitrotoluene-2-sulfonic acid containing solution; and
   f) condensing the neutralized 4-nitrotoluene-2-sulfonic acid in the presence or absence of the amine liberated in the basefying step.

2. A process for preparing the dye Direct Yellow 11 (C.I. 40000), which comprises:
   a) sulfonating nitrotoluene with oleum, thereby preparing 4-nitrotoluene-2-sulfonic acid;
   b) diluting the solution containing said 4-nitrotoluene-2-sulfonic acid with water;
   c) partially neutralizing the 4-nitrotoluene-2-sulfonic acid to 50–70% neutralization with added mineral base;
   d) extracting the partially neutralized 4-nitrotoluene-2-sulfonic acid with a lipophilic amine;
   e) basefying the aqueous, 4-nitrotoluene-2-sulfonic acid containing extract solution with aqueous alkali metal hydroxide solution;
   f) heating the mixture to a temperature from 50–100° C.;
   g) subsequently acidifying and, after thorough mixing and phase separation, removing the aqueous phase; and
   h) extracting the dye which is present in the organic phase with water and water-miscible amines, removing the aqueous phase, neutralizing, and isolating the dye present therein.

3. The process of claim 2, wherein said alkali metal hydroxide solution is a sodium hydroxide solution.

4. In a method of preparing the dye Direct Orange 15 by condensing nitro-o-toluenesulfonic acid in an alkaline solution containing a reducing agent, the improvement comprising:
   employing, as the nitrotoluenesulfonic acid reactant, the amine salt of 4-nitrotoluene-2-sulfonic acid product produced by the process of claim 1.

* * * * *

UNITED STATES PATENT AND TRADEMARK OFFICE
CERTIFICATE OF CORRECTION

PATENT NO. : 6,160,169

DATED : December 12, 2000

INVENTOR(S): Rudolf BERMES, et al.

It is certified that an error appears in the above-identified patent and that said Letters Patent is hereby corrected as shown below:

On the title page, item [62] and first paragraph of Column 1, the Related U.S. Application Data is missing. Item [62] should read as follows:

Related U. S. Application Data

--[62] Division of application Serial No. 08/987,605, filed on December 9, 1997, now Pat. No. 5,892,105--

--Also--

Column 1, first paragraph, the Related U.S. Application Data has been omitted. The paragraph should read as follows:

--This application is a Division of application Ser. No. 08/987,605, filed on December 9, 1997, now U.S. Pat. No. 5,892,105--

Signed and Sealed this

First Day of May, 2001

Attest:

NICHOLAS P. GODICI

*Attesting Officer*   *Acting Director of the United States Patent and Trademark Office*